Figure 1:
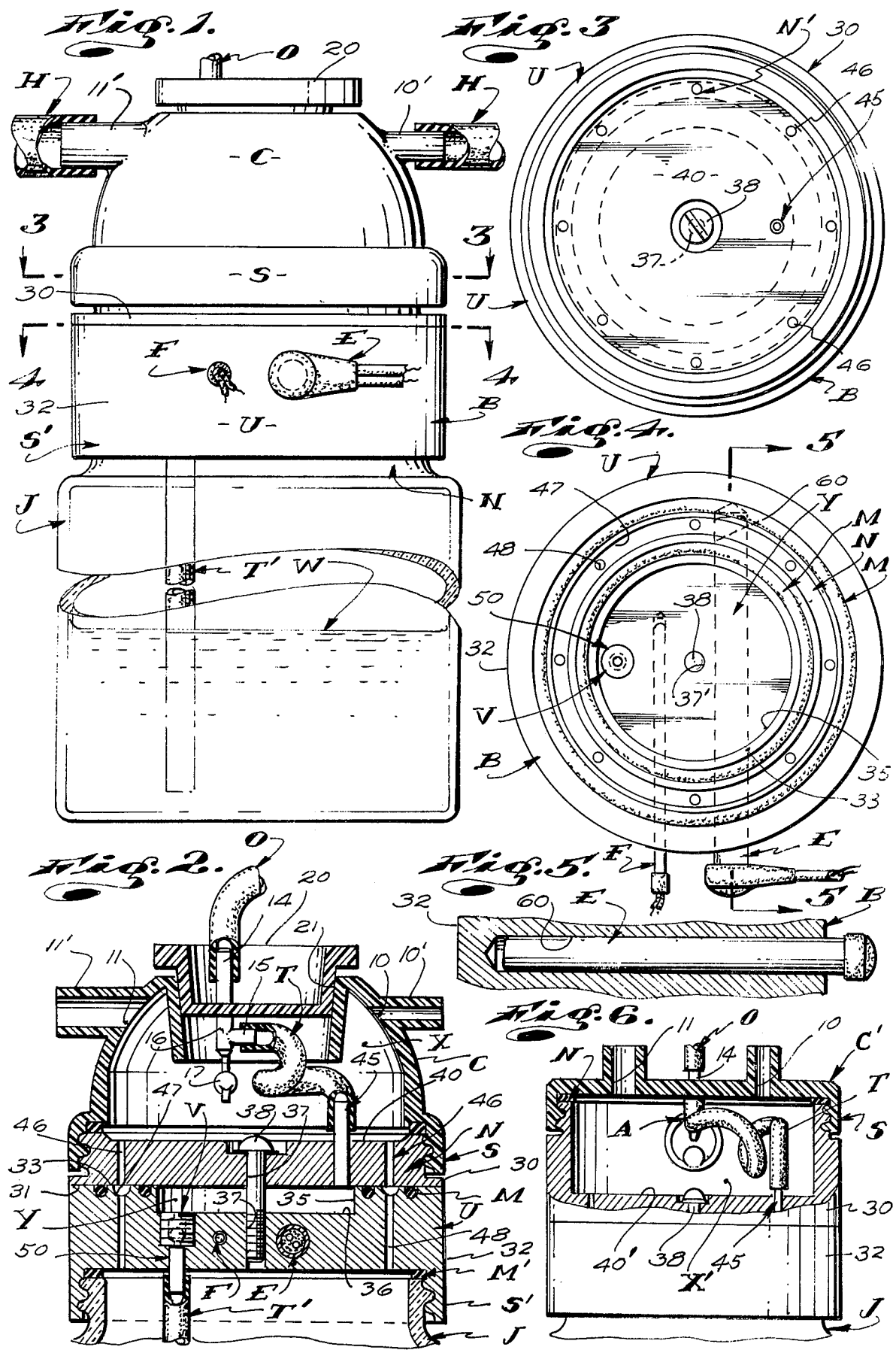

United States Patent [19]

Williams

[11] 4,101,611
[45] Jul. 18, 1978

[54] NEBULIZER

[75] Inventor: David E. Williams, Hemet, Calif.

[73] Assignee: Amark Industries, Inc., San Jacinto, Calif.

[21] Appl. No.: 766,263

[22] Filed: Feb. 7, 1977

[51] Int. Cl.² .................. B01F 3/04; A61M 15/00
[52] U.S. Cl. .................. 261/142; 128/193;
219/273; 219/275; 239/138; 261/78 A; 261/DIG. 65
[58] Field of Search ............ 261/78 A, 142, DIG. 65; 23/272.7; 128/192-194; 219/271-276; 239/135-139

[56] References Cited

U.S. PATENT DOCUMENTS

| | | | |
|---|---|---|---|
| 1,254,348 | 1/1918 | Palmer | 261/142 |
| 2,040,630 | 5/1936 | Silten | 128/193 X |
| 3,353,536 | 11/1967 | Bird et al. | 23/272.7 X |
| 3,384,103 | 5/1968 | Lansky | 261/78 A X |
| 3,515,676 | 6/1970 | Hierta et al. | 261/78 A X |
| 3,859,398 | 1/1975 | Havstad | 128/193 X |
| 3,990,441 | 11/1976 | Hoyt et al. | 261/DIG. 65 |
| 4,009,713 | 3/1977 | Simmons et al. | 261/DIG. 65 |

FOREIGN PATENT DOCUMENTS 167,879  8/1921  United Kingdom .............. 261/142

*Primary Examiner*—Richard L. Chiesa
*Attorney, Agent, or Firm*—Georges A. Maxwell

[57] ABSTRACT

A nebulizer comprising a container with a supply of water, a downwardly opening cap with air delivery means and housing an aspirator connected with a supply of oxygen under pressure and adapted to draw water from said supply, an elongate heating unit with an upper end defining a heating chamber and carried by the container, said cap engaged with the upper end of the unit to define a mixing chamber of fixed predetermined volume and shape in which the aspirator is positioned, water inlet means communicating with the heating chamber and water supply, water outlet means communicating with the heating chamber and the aspirator and an electric resistance heater in the unit, spaced from the heating chamber to heat water in the heating chamber and temper the atmosphere in the mixing chamber.

17 Claims, 8 Drawing Figures

NEBULIZER

This invention has to do with an improved means for tempering and humidifying the oxygen-enriched air for delivery to a person requiring respiratory aid and which is of that type or class of means commonly referred to as a nebulizer in the medical arts.

Nebulizers provided by the prior art are commonly provided with or include a jar-like container in which a supply of water is deposited, a closure or cap engaged on and closing the upper open end of the container, a resistance heater unit carried by the cap and depending into the container and into the water therein to temper the water, an aspirator carried by the cap to occur within the container, above the water therein and having an inlet connected with a supply of oxygen under pressure, a suction hose extending from the aspirator into the supply of water and a diffuser onto which oxygen and water issuing from the aspirator impinge. The cap is provided with an outlet which connects with a delivery hose extending to the person to be supplied with tempered, humidified oxygen. In addition to the above, the caps are commonly provided with diluting means which serve to combine air with the tempered and humidified oxygen and which include air metering valves related to the caps and which operate to admit air into the containers at predetermined volumes and rates.

While the above, rather fundamental or basic, form of nebulizer has been found acceptable and is in wide use, the most often noted objection resides in the relationship of the resistance heater and water supply. That is, that relationship of parts wherein the resistance heater is immersed in and is in direct contact with the water supply. Such a relationship is considered dangerous and highly undesirable by many physicians and technicians. Such a relationship of parts not only presents a risk of short-circuiting and electrical shock, but prevents the possibility of placing many medical additives into the water which would be subject to adverse effects when and if brought into direct contact with the heated surface of the heaters.

Another shortcoming found to exist in nebulizers of the general character referred to above resides in the fact that the power demands and heat output of the heaters is not constant but varies widely in response to variations in the volumes of water in the containers. When a container has a full supply or large volume of water and the heater is substantially fully submerged therein, the heat output demand and the power demand placed upon the heater is materially different from those demands placed upon the heater when the water supply has been reduced or nearly exhausted and a small part or portion of the heater remains submerged in the water. The heat demand and power requirements of the heater is also materially affected by the outside area of the container and the heat exchange effected thereby with ambient atmosphere. Such heat exchange is effected and varies widely in response to the changing volumes of water and air in the containers.

While means have been provided to control the heat output of heaters in the ordinary nebulizers provided by the prior art whereby substantially uniform temperature of the water in the containers is attained, the results are not wholly satisfactory and can best be described as being in the nature of a compromise between full or accurate control and no control at all.

Another shortcoming to be found in the ordinary nebulizer of the character referred to above resides in the fact that the upper portion of the container, between the cap and water supply and in which oxygen, water and air are mixed, and which is subject to changing and increasing in volume or size as the water supply is diminished, is a condensing chamber and is such that much of the water mixed with the air and oxygen by the aspirator is permitted to precipitate and/or drop out of the oxygen and/or air, before it can be conducted into the hose for delivery to the patient. As the supply of water decreases and the mixing space in the container above the water increases, more water precipitates and/or drops back into the water supply and the tempered humidified oxygen or oxygen and air delivered by the nebulizer becomes progressively drier.

Yet another shortcoming found in the ordinary nebulizer of the character referred to above resides in the fact that the nebulizers must be regularly and systematically cleaned and sterilized. Such cleaning and sterilization often requires that all of the components, including the resistance heater, be placed in autoclaves and subjected to high temperatures and pressures for predetermined periods of time. While the resistance heater structures employed in such apparatus are intended to withstand such temperature and pressure conditions, they are also subject to breaking down or failing under such conditions. It is believed clear and apparent that although a structure is made so that it should withstand certain abuses, it is imprudent to subject such a structure to such abuses unnecessarily. In accordance with the above, while the resistance heaters are intended to withstand the abuses of the cleaning practices to which nebulizers and/or their components are subjected, it is recognized that best practice demands that the heaters not be subjected to such abuses and that their durability and safety factors not be unnecessarily taxed and tried.

In the art, the delivery of tempered, humidifed oxygen or oxygen-enriched air to a patient is oftentimes controlled to be intermittent. That is, it is started and stopped synchronously with inspiring and expiring of the patient. Such intermittent delivery is either voluntary or involuntary, that is, delivery starts and stops in response to the demand of the patient or in involuntarily started and stopped in response to some means external or separate from the patient and which serves to force and pace the patient's respiration. In either event, the control or starting and stopping of delivery is commonly effected by starting and stopping the flow or supply of oxygen, from its source, as by means of an automatically controlled on and off valve.

The ordinary nebulizer is noticeably less satisfactory and quite ineffective when the delivery of conditioned oxygen or oxygen-enriched air to a patient is intermittent since each time delivery is stopped, the flow of oxygen to the nebulizer is stopped, and the apparatus is momentarily shut down. Also, each time delivery is commenced, the nebulizer must be set or put back into operation.

The above is due to the fact that in most nebulizers, the oxygen is introduced into the nebulizers through the aspirators with which the suction hoses depending into the water supply are connected. The flow of oxygen through the aspirators establish minus pressures which draw water up through the hoses and introduce the water into the jets of oxygen issuing from the aspirators. It is believed obvious that if the flow of oxygen is intermittent, each time the flow of oxygen is stopped the flow of water in the suction hoses not only stops, but reverses and requires that the flow and full supply of water in the suction hoses be reestablished each time the flow of oxygen into and through the aspirators is reestablished.

In addition to the foregoing, and due to the rather large volume of the mixing chambers or spaces in which the oxygen, water and air are mixed in ordinary nebulizers, uniform and effective circulation of gases and vapors into, within and from the mixing chambers or spaces is seldom uniformly maintained.

An object and feature of the present invention is to provide an improved nebulizer including a lower water supply chamber, an upper mixing chamber with a discharge port, an oxygen and water receiving and discharging aspirator within the mixing chamber, a heating unit of heat conducting material defining a water heating chamber interposed between the water supply and mixing the chamber and including water conducting means between the water supply and the aspirator; and an electric resistance heater unit engaged within the said unit and isolated from the water supply and from each of said chambers.

Another object and feature of this invention is to provide a heating unit which is compatible and engageable with and between a standard commercially available aspirator water supply container and a standard commercially available aspirator container engaging cap structure having aspirating means, oxygen supply connecting means, air supply means and outlet or delivery means.

Yet another object of the invention is to provide a heating unit of the general character referred to which cooperates with a related cap structure of the character referred to above to establish a mixing chamber of limited, constant or uniform volumetric extent and configuration whereby constant and uniform mixing of water, vapor and gases is substantially assured and which is sufficiently small so that excessive, premature precipitation of water within the chamber prior to delivery to a patient cannot occur.

Still another object and feature of this invention is to provide a heting unit of the general character referred to having drain means to drain free water in the above noted mixing chamber into the container related to the heating unit and having a small water heating chamber whereby only that small volume of water required to temper the oxygen and air delivered by the nebulizer is heated and to thereby reduce the heat demand and power consumption made upon the heater related to the heating unit.

Another object and feature of the present invention is to provide a heating unit having upwardly and downwardly extending water outlet and inlet openings communicating with the water heating chamber, means to connect to the outlet opening with a water supply of the aspirator and a suction hose connected with the inlet opening and which extends downwardly into the water supply in the container with which the heating unit is related.

A further object of my invention is to provide a heating unit of the character referred to which is provided with check-valve means at the inlet opening to prevent water from dropping or flowing back and out of the heating chamber during operation of the nebulizer for intermittent delivery of tempered, humidified oxygen or oxygen-enriched air from the nebulizer.

It is another object of the invention to provide a heating unit of the character referred to which includes a large mass of heat conducting metal about and defining at least part of the water heating chamber and which has an elongate opening, with an outer open end extending into it in spaced relationship from the heating chamber and into which an elongate cartridge type resistance heater is normally removably engaged. In practice, said heater can be slidably engaged in the said opening when the structure is cold and tightly engaged in said opening when the structure is heated and caused to expand.

It is an object and feature of the invention to provide a heater unit which has a large surface defining a portion of the mixing chamber whereby the heating unit serves to temper the mixing chamber and the materials mixed therein and serves to increase the efficiency and uniformity of operation of the construction.

Finally, it is an object and feature of the present invention to provide a nebulizer structure of the general character referred to wherein the structure defining the heat chamber is sectional and wherein substantially all elements, parts and means going to make up the structure can be easily and conveniently assembled and disassembled for effective and economical servicing of the construction.

The foregoing and other objects and features of this invention will be fully understood from the following detailed description of a typical preferred form and application of the invention, throughout which description reference is made to the accompanying drawing in which:

FIG. 1 is an elevational view of a nebulizer embodying the present invention;

FIG. 2 is a detailed sectional view of a portion of the structure shown in FIG. 1;

FIG. 3 is a view taken substantially as indicated by line 3—3 on FIG. 1;

FIG. 4 is a sectional view taken substantially as indicated by line 4—4 on FIG. 1;

FIG. 5 is a sectional view taken as indicated by line 5—5 on FIG. 4;

FIG. 6 is a sectional view of a modified form of the invention;

FIG. 7 is a partial sectional view of another modified form of the invention; and FIG. 8 is a view similar to FIG. 7 showing yet another form of the invention.

One basic form of aspirator provided by the present invention includes a standard upwardly opening jar-like container J with an externally threaded neck N and in which a supply of water W is deposited, a cap C normally engageable with the neck of the container and a novel heating unit U, as provided by the present invention, engaged with and between the container J and the cap C.

The cap C is a molded plastic structure characterized by a dome-like top portion defining a downwardly opening semi-hemispherical mixing chamber X. The cap C is further characterized by an internally threaded annular skirt S about the lower perimeter of the said top portion and adapted to normally engage the neck N of the container J, with the chamber X in communication with and establishing an upper extension of the interior of the container.

The cap C is preferably provided with a suitable sealing means M to seal about the upper rim or edge portion of the neck N and has lateral inlet and outlet ports 10 and 11 with outwardly projecting hose coupling nipples 10' and 11' in its upper dome-like portion, communicating with the chamber X and normally connected with delivery and air supply hoses H and H'

The delivery hose H extends to a patient and is connected with other related delivery means (not shown). The air hose H' extends to and is connected with an air metering or dilution valve (not shown), which serves to control and effect any desired volume and/or flow of ambient air into the chamber X, as desired or as circumstances require.

In addition to the above, the cap C includes an aspirator A. The aspirator A is located within the chamber X and includes an oxygen coupling means 14, a water supply means 15, a nozzle 16 and a diffuser 17. The means 14 includes a nipple which communicates with the nozzle and extends through the cap to the exterior of the structure and connects with an oxygen supply tube O extending from a high-pressure oxygen supply (not shown). The means A includes a nipple 15 accessible within the chamber X and with which the upper end of a water suction tube T is connected. The tube T, in accordance with prior art, would ordinarily extend downwardly into the container J and the water supply W therein. In the instant case, the tube T remains wholly within the confines of the cap and connects with the unit U, as will hereinafter be described.

In the case illustrated, the aspirator A is carried by a tapered plug 20, removably, sealingly engaged in a tapered access opening 21 provided in the top portion of the cap, as clearly illustrated in the drawings.

The aspirator A is such that oxygen delivered to it, through the tube O and issuing from the nozzle 16, draws a vacuum or minus pressure at the nipple 15 to draw water upwardly through the tube T and into the flow stream of oxygen. The water and oxygen issue from the nozzle 16 and impinge upon the diffuser 17 within the chamber X to atomize and mix the oxygen and water together and to mix the oxygen and water with that air which is introduced into the chamber X through the port 11, under control of the above mentioned dilution valve (not shown).

It should be noted at this time that in practice, the provision and/or utilization of the dilution valve mentioned in the foregoing and the delivery of air into the mixing chamber X is not always provided and when provided, is not always used.

The container J and cap structure C thus far described is essentially that standard, commercially available nebulizer which is disclosed in U.S. Pat. No. 3,353,536 and sold under the tradename Bird by Bird Corporation in the City of Palm Springs, California.

Those differences which may be found to exist between the structure illustrated and the structure disclosed in the above noted patent pertain to matters of structure which in no way affect the novelty and/or spirit of the present invention and have been adopted for the purpose of simplification and more clear disclosure of the present invention.

The heating unit U here provided is an elongate vertically extending cylindrical unit characterized by an upwardly projecting externally threaded reduced neck portion N' corresponding in axial and external extent and configuration with the neck N of the container J, a central cylindrical body portion B and a lower internally threaded angular skirt S' corresponding in axial and internal extent and configuration with the skirt S of the cap C. Sealing means M' corresponding to the above noted sealing means M is related to the body and/or skirt S'.

With the unit U thus far described, it will be apparent that the unit U is in the nature of an insert and is such that it can be and in practice is cooperatively engaged with and between the cap C and container J in threaded and sealed relationship therewith, as clearly illustrated in the drawings.

The body B of the unit U is sectional and includes an upper section 30 with a flat, horizontal bottom surface 31 and a lower section 32 with a flat, horizontal top surface 33. The surfaces 31 and 33 normally establish flat bearing and heat conducting contact with each other.

The lower section 32 has a central, upwardly opening cylindrical bore 35 of limited vertical extent or depth, terminating at a flat bottom 36 within the section 32 and cooperating with the upper section to define a water heating chamber Y.

The sections 30 and 32 have central, vertical, axially aligned clamp screw receiving openings 37 and 38 through and into which an elongate clamp screw 38, accessible at the top of section 30, is engaged releasably to hold the sections of the unit in tight clamped relationship with each other. The screw 38 extends freely through the chamber Y, as clearly illustrated.

In practice, and as shown in the drawings, the top central portion of the upper section can be recessed as at 40 to establish a catch basin.

It is to be noted that the top of the unit U cooperates with the cap C to establish the aforementioned mixing chamber X and that the chamber X, being separated from the container J, is in no way affected by changes in level of water in the container and remains constant in size and configuration, whereby uniform continuous mixing of oxygen, water and air is assured.

In addition to the above, the upper section 30 of the unit U has water delivery means 45 to connect the chamber Y with the suction tube T in the chamber X. The means 45 is shown as including a vertical flow tube engaged through an opening in the top of the unit to communicate with the top of the chamber Y and projecting from the top of the unit into the chamber where it establishes a nipple with which the lower end of the tube T is engaged or coupled.

Finally, the upper section 30 is provided with one or a plurality of circumferentially spaced vertical drain or through openings 46, the axes of which are spaced radially between the chamber Y and the exterior of the unit.

The lower section 32, in addition to the aforementioned bore 35 and opening 37, is provided with an upwardly opening annular groove or drain galley 47 which normally communicates with the lower ends of the openings 46 in the upper section 30 and one or a plurality of circumferentially spaced vertical drain or through openings 48 extending from the galley and opening at the bottom of the unit, in communication with the interior of the container J.

The section 32 next includes sealing means M to seal with the section 30 and which is shown as including an upwardly opening annular groove spaced radially inwardly and outwardly of the galley 47 and O-ring seals in the grooves to normally seal therein and with the bottom 31 of the upper section 30.

The section 32 next includes water receiving means 50 to connect the chamber Y with the upper end of a secondary, vertical, suction tube T' extending from the unit U into the chamber J and into the supply of water W wherein. The means 50 is shown as including a vertical flow tube engaged through an opening in the section 32 to communicate with the bottom of the chamber Y and projecting downwardly therefrom into the container to establish a nipple with which the upper end of the tube T' is engaged or crippled.

In addition, if desired, a check valve means V is provided at the upper end of the means 50 to prevent the downward flow and/or draining of water from the chamber Y. The means V can, as shown, include a simple ball-check valve unit engaged in an enlarged bore in the upper end of the opening of the means 50 to occur at the bottom of the chamber and immediately above the upper end of the flow tube of said means.

The unit U next includes an elongate receiver opening 60 entering the exterior of the body and in which an elongate cartridge type resistance heater E is slidably engaged.

In the case illustrated, the opening 60 extends horizontally into the lower section 32 of the unit in spaced relationship below the chamber Y and is offset, on a cord-line, to clear the opening 37 and the clamp screw 38 engaged therein. The opening 60 enters one side of the unit and preferably, though not necessarily, stops short of the other side of the unit and is blind.

The heater E is an elongate cylindrical metal jacketed cartridge-type heater unit with inner and outer ends. The heater can be such that when the section 32 and heater are cool, the heater slidably engages in the opening 60 and such that when the structure is heated and expands, tight heat conducting contact is established therebetween.

The outer end of the heater is provided with suitable conventional electrical coupling means to connect the heater with any desired and suitable power supply and/or control means (not shown).

The heater E is designed and/or selected so that a desired, suitable, predetermined heat output and rate of power consumption can be attained.

In addition to the foregoing, the heater E can include a suitable thermocouple means to effect desired control of electric heating means. As illustrated, a separate thermocouple and/or thermal fuse means F can be related to the unit in substantially the same manner as the heater H. That is, an elongate cylindrical probe-type thermocouple and/or fuse can be engaged in an opening entering one side and extending into the body of the unit, as clearly illustrated in the drawings.

In the construction described above, the chamber X is defined primarily by the semi-hemispherical interior of the cap C. In practice, and as illustrated in FIG. 6 of the drawings, if a flat disc-like cap C' is employed, the necessary mixing chamber X' can be established by increasing the vertical extent of the upper section 30' of the unit U' and establishing a large or deep chamber defining basin 40' in the upper end of the section 30'. In all other respects, the above noted modified form of the invention can remain essentially the same as the first described form of the invention, so far as the idea of means is concerned.

It will be readily apparent that the chamber X defined by the cap C and the unit U is of limited predetermined volume configuration and is such that operating conditions or the atmosphere within the chamber remain the same or constant when the construction is in operation. The conditions within the chamber X are in no way altered, affected or modified by the level of water in the container and/or the change of the unoccupied space in the container as the water level therein drops or changes. The size or volume of the chamber X, being invariable, can be and is established so that a most effective and efficient tempering and humidifying of gases is effected and is not so large that undesired and/or excessive separation or precipitation of water, from the gases within the chamber, can take place before the humidified gases are conducted out of the chamber for delivery to a patient.

In addition to the above, it will be apparent that the top of the heater unit U defines the bottom of the chamber X and serves to heat and temper the interior of the chamber and prevents or overcomes keeling of the bases and water within the chamber caused by expansion of the oxygen at the aspirator, the drawing in of keeled diluting air and other like factors.

That water which drops out or precipitates in the chamber, into the basin 40 of the unit U, is conducted back into the container J through the drain means established in the unit U by the openings 46 and 48. That water which drains back into the container is heated when in the chamber and is further heated when it flows down through the drain opening in the unit, whereby said drain water tends to pre-temper or remove any chill from the water supply W within the container. As a result of the above, the heat energy stored and/or carried by the drain water is put to beneficial use and reduces the heat and energy demands made upon the heater E.

The chamber Y within the unit U is a small chamber of predetermined, limited, volumetric extent. The volumetric extent of the chamber Y is determined by the overall mass of the unit U, the coefficient of heat conductivity of the material from which the unit is established, the heat output rating of the heater E, the mean differential temperature of the supply water W entering the chamber and of the heated water flowing from the chamber and the volume or rate of flow into and out of the chamber. In practice, the volume of the chamber Y may be about one ounce.

In operation, the chamber is maintained full of water at all times and is such that complete uniform heating of the water is assured and is in no way interfered with, as by the introduction of air or gases in the chamber.

In practice, the flow tubes of the means 45 and 50 are established of heat conducting metal whereby heating of the water commences when the water first reaches the tube 50 and continues until the water leaves the tube 45.

The check valve V serves to prevent water in the chamber from draining from the chamber, as when the structure is operated intermittently. The valve, when closed, also prevents water in the tubes T and T' from draining downwardly therein or therefrom.

As a result of the above, if the structure is temporarily put out of operation, it remains constantly primed and ready to deliver water, at the aspirator A, immediately upon reestablishment of operation.

The heater E, engaged in the opening 60 in the body B of the unit U, is isolated from the water and/or gases whereby the danger of shorting out, as a result of water leakage and the like, is eliminated. Further, since the heater is isolated from all interior surfaces of the construction which are contacted with or exposed to the water and gases handled by the construction, the necessity of subjecting the heater E to other than minimal wiping and cleaning services is eliminated.

A novel feature of the invention resides in the fact that the heater E is frictionally slidably engaged in the opening 60 when the construction is cool and becomes snug or tightly engaged in the opening when the construction is heated. Accordingly, the provision of special retaining means to hold the heater engaged in the unit can be eliminated. (In practice, it is anticipated that suitable special retaining means will be specified and required, in spite of the fact that they are considered nonessential).

In conclusion, it will be apparent that the present invention, in essence, resides in the provision of a water heating unit of the general character referred to above which is such that it can be effectively related to and with existing nebulizer structures to effect modification of such structures whereby preexisting shortcomings to be found therein are eliminated and whereby the operating effectiveness and efficiency of the structures is materially enhanced. Units U, established in accordance with the teachings and spirit of our invention can be provided for substantially all commercially available nebulizer structures or, if desired, can be established for use in connection with new vessels, caps and related nebulizer means and structure designed especially therefor.

In FIG. 7 of the drawings, the sectional metal heating unit $U^2$ is a simple plug-like unit with a straight cylindrical exterior and flat top and bottom ends. The unit $U^2$ is arranged centrally within an elongate vertically extending tubular plastic insert or adapter $P^2$ with upper and lower threaded end portions to cooperatively engage the threaded parts or portions of related nebulizer caps and containers. The unit $U^2$ is shown oriented in the plastic insert P by means of a shoulder within the insert and is releasably retained in there as by means of a snap ring, whereby the unit $U^2$ can be easily and conveniently removed for cleaning and servicing purposes and the like.

In this last form of the invention, the water delivery means $45^2$ is arranged concentric with the rotative axis of the related threaded cap, whereby coupling can be established with the aspirator $A^2$ and assembly of the construction can be made more simple. To this end, the central clamp screw $38^2$ has a central flow passage, a lateral port establishing communication between the flow passage and the chamber $Y^2$ and an upwardly projecting fluid conducting stringer adapted to slidably and rotatably enter an axially aligned, downwardly opening water inlet opening provided in the aspirator structure with the related cap $C^2$.

The unit $U^2$ fits loosely in the insert P so as to define an annular drain passage longitudinally of and about the exterior of the unit. Such an annular drain passage means is substituted for and serves the same function as the openings 46, galley 47 and openings 48 provided in the first form of the invention.

In all other respects, the structure shown in FIG. 7 and briefly described above is essentially the same as that in the previously described forms of the invention so far as the fundamental structure and rule of action thereof is concerned.

Figure 8:
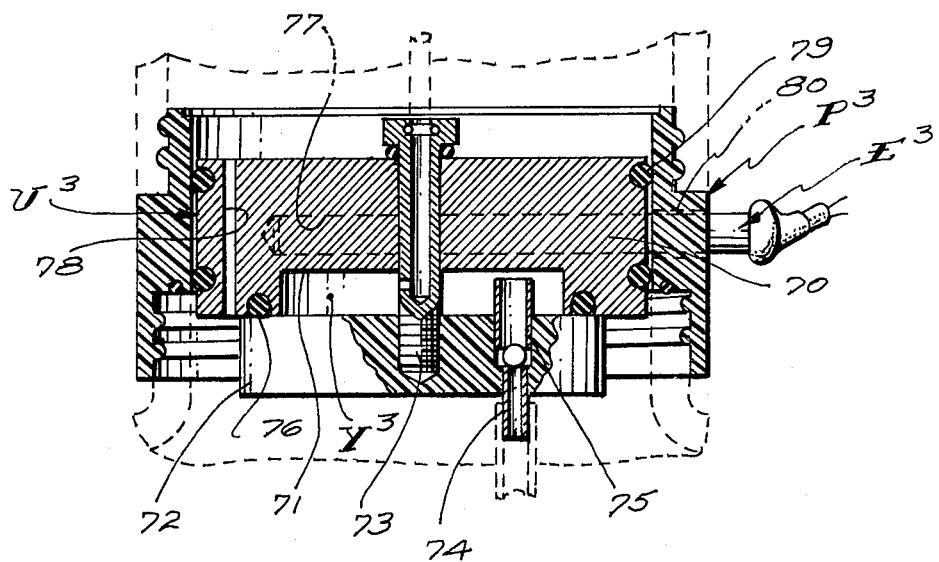

In FIG. 8 of the drawings, I have shown another form of the invention similar to the last noted form of the invention shown in FIG. 7.

In the form of the invention shown in FIG. 8, the unit $U^3$ includes an upper metal section 70 in which the chamber $Y^3$ is defined by a bore 71. The bore 71 is closed by a disc-like plastic lower section 72 releasably secured in place by a central clamp screw 73 carried by the section 70, as shown. The lower section 72 carries and/or accommodates water inlet means 74 and valve means 75 similar to the means 45 and valve means V in the first form of the invention. A O-ring sealing means 76 is provided between the sections 70 and 72, as shown.

The upper section 70 is provided with an opening 77 similar to the opening 60 in the first form of the invention and in which an elongate cartridge or similar type of resistance heater $E^3$ is engaged.

The clamp screw 53 is provided with an upwardly opening central flow passage and a lateral port establishing communication between the chamber $Y^3$ and the passage. The passage is adapted to slidably and rotatably receive a concentric, depending, fluid conducting stinger or the like, provided on the aspirator which is to be related to the unit $U^3$ (not shown).

The upper section is greater in diameter than the lower section and the outer peripheral portion of the upper section which project radially outwardly from the lower section is provided with vertical through opening or drain means 78.

The upper section 70 has a straight cylindrical exterior with a pair of vertically spaced annular grooves, occurring above and below the opening 77 and in which O-ring seals 79 are engaged.

The unit $U^3$ is slidably engaged into a straight cylindrical opening or bore in a plastic cap and vessel engaging insert $P^3$ similar to the plastic insert P in the last described form of the invention. The seals 79 seal between the insert and the top section of the body above and below the opening 77 and heater $E^3$ yieldingly retain it in position in the insert. The heater $E^3$ has an outer end portion which projects outwardly through an opening 80 in the insert and which cooperates with the insert to lock the unit in axial position in the insert.

It will be apparent from the above that in putting this invention into practice, both sections of the heating unit need not be of metal; the cavity can be defined by a bore in either the upper or lower section and the cartridge heater can be in either the upper or lower section, without departing from the spirit of the invention.

Figure 2:
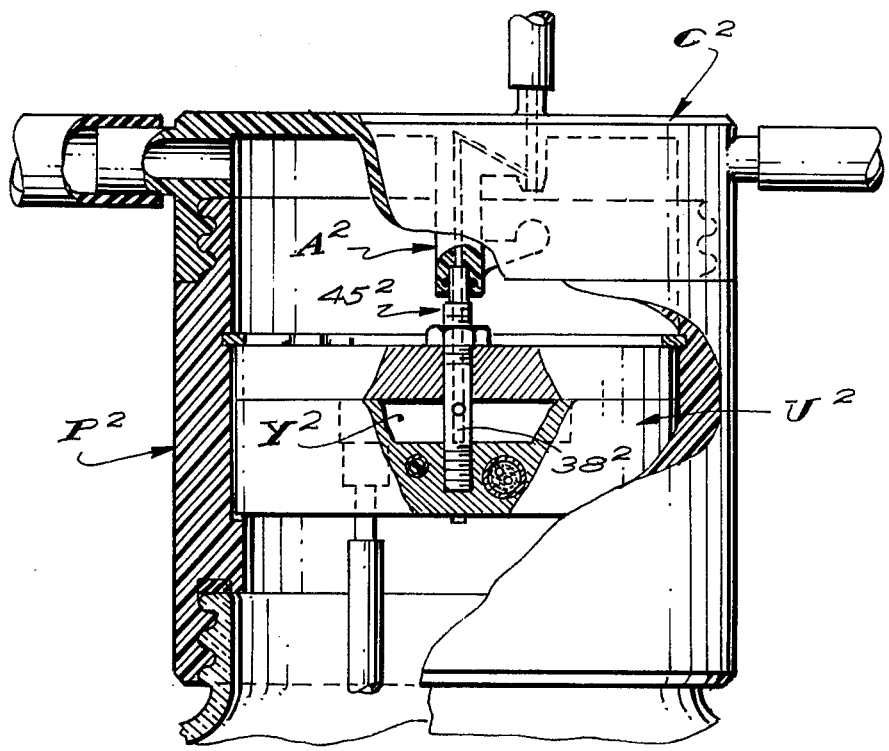

It will be apparent from the foregoing that the outer peripheral portion of the lower section of the unit U shown in FIG. 2 of the drawings could be established by a cylindrical plastic sleeve or jacket and that the lower internally threaded skirt portion could be defined by an extension of the plastic sleeve or jacket. The above is also true with respect to the upper section of the unit U, that is, the upper section of the unit U could also be provided with an exterior plastic sleeve or jacket and that sleeve or jacket could extend upwardly to establish the threaded portion of that section of the unit.

The provision of the above noted plastic adapters in which the sectional heating unit is engaged or the provision of plastic sleeves or jackets about the exterior of the sections of the unit affords the obvious advantage of heat insulating the heating units from ambient atmosphere; electrically insulating the exterior of the units and rendering the units sparkproof and safe for use in operating rooms and the like. Making the threaded ends and/or portions of the structure that we provide of plastic renders the resulting structure more compatible with mating threads of related nebulizer caps and vessels or containers established of plastic, glass or other material, the coefficient of expansion which is materially different than that of the metal from which the sections of the heating unit are made.

Still further, the employment of plastic, as noted and suggested above, affords for easy and economical molding of the threaded portions of the construction, eliminating the necessity of machining the threads in the metal sections of the construction and thereby simplifying and reducing the cost of manufacture.

Having described only typical preferred forms and applications of my invention, I do not wish to be limited to the specific details herein set forth, but wish to reserve to ourselves any modifications and/or variations that may appear to those skilled in the art and which fall within the scope of the following claims.

Having described my invention, I claim:

1. An elongate vertical water heating unit of heat conducting and storing material in combination with a fluid container having an upper open end and a supply of water within and with a container cap with an air supply means, air delivery means and aspirator means to draw water from said supply and connected with a supply of oxygen under pressure; said unit having upper and lower ends and a water heating chamber in spaced relationship between said upper and lower ends, coupling means at the lower end of the unit coupling the upper end of the container with said unit, coupling means at the upper end of the unit coupling said cap with said unit, said unit and cap cooperating to define a mixing chamber in which said aspirator means is positioned and with which said air supply and delivery means communicate, a water inlet means between the heating chamber and the water supply, water outlet means between the heating chamber and said aspirator means, a heater opening entering one side of and extending into the unit between the upper and lower ends thereof and in spaced relationship from said heating chamber and from said water inlet and outlet means and a resistance heater positioned in said opening, said heater having means at the exterior of the unit connected with the power supply, said heater heating said unit to heat the water in the heating chamber and to temper the atmosphere in said mixing chamber.

2. The structure set forth in claim 1 wherein said unit comprises upper and lower sections with top and bottom surfaces, said sections arranged with the bottom surface of said upper section and top surface of said bottom section in opposed engagement with each other, one section having a central bore opening toward the other section, said bore and other section defining said heating chamber, sealing means between the sections and spaced radially outward of said heating chamber and screw means releasably securing the sections together.

3. The structure set forth in claim 2 wherein said heater opening is an elongate opening entering one of said sections from one side thereof between the upper and lower surfaces thereof and extending uninterruptedly inwardly therein.

4. The structure set forth in claim 3 wherein said water inlet means includes an inlet opening in said lower section communicating with the heating chamber and a fluid conductor extending from that opening into the water supply, said water outlet means including an outlet opening in the upper section communicating with the heating chamber and a fluid conductor between that opening and the aspirator.

5. The structure set forth in claim 2 wherein said water inlet means includes an inlet opening in said lower section communicating with the heating chamber and a fluid conductor extending from that opening into the water supply, said water outlet means including an outlet opening in the upper section communicating with the heating chamber and a fluid conductor between that opening and the aspirator.

6. The structure set forth in claim 1 wherein said unit comprises upper and lower sections with opposing surfaces, one section having a central bore opening toward the other section, said bore and other section defining the heating chamber, said water inlet means includes an inlet opening in said lower section communicating with the heating chamber and a fluid conductor extending from that opening into the water supply, said water outlet means including an outlet in the upper section communicating with the heating chamber and a fluid conductor between that opening and the aspirator.

7. The structure set forth in claim 1 wherein said unit includes drain means to drain water in the mixing chamber downwardly into the container and including a vertical drain opening in and through the unit communicating with the mixing chamber and the interior of the container.

8. The structure set forth in claim 7 wherein said unit comprises upper and lower sections with top and bottom surfaces, said sections arranged with the bottom surface of said upper section and top surface of said bottom section in opposed engagement with each other, one section having a central bore opening toward the other section, said bore and other section defining said heating chamber, sealing means between the sections and spaced radially outward of said heating chamber and screw means releasably securing the sections together.

9. The structure set forth in claim 8 wherein said heater opening is an elongate opening entering one of said sections from one side thereof between the upper and lower surfaces thereof and extending uninterruptedly inwardly therein.

10. The structure set forth in claim 9 wherein said water inlet means includes an inlet opening in said lower section communicating with the heating chamber and a fluid conductor extending from that opening into the water supply, said water outlet means including an outlet opening in the upper section communicating with the heating chamber and a fluid conductor between that opening and the aspirator.

11. The structure set forth in claim 10 wherein said water inlet means includes an inlet opening in said lower section communicating with the heating chamber and a fluid conductor extending from that opening into the water supply, said water outlet means including an outlet opening in the upper section communicating with the heating chamber and a fluid conductor between that opening and the aspirator.

12. The structure set forth in claim 8 wherein said water inlet means includes an inlet opening in said lower section communicating with the heating chamber and a fluid conductor extending from that opening into the water supply, said water outlet means including an outlet opening in the upper section communicating with the heating chamber and a fluid conductor between that opening and the aspirator.

13. The structure set forth in claim 1 wherein said water inlet means includes an inlet opening in the unit communicating with the mixing chamber and a fluid conductor depending from the unit into the water supply in the container and a check valve in the inlet opening to check the flow of water from the chamber into and through said inlet opening, said outlet means including an outlet opening in the unit communicating with the mixing chamber and a water conductor between said aspirator and outlet opening.

14. The structure set forth in claim 13 wherein said unit includes drain means to drain water in the mixing chamber downwardly into the container and including a vertical drain opening in the unit communicating with the mixing chamber and the interior of the container.

15. The structure set forth in claim 14 wherein said unit comprises upper and lower sections with top and bottom surfaces, said sections arranged with the bottom surface of said upper section and top surface of said bottom section in opposed engagement with each other, one section having a central bore opening toward the other section, said bore and other section defining said heating chamber, sealing means between the sections and spaced radially outward of said heating chamber and screw means releasably securing the sections together.

16. The structure set forth in claim 13 wherein said unit comprises upper and lower sections with opposing surfaces, one section having a central bore opening toward the other section, said bore and other section defining the heating chamber, said heater opening is an elongate opening entering one of said sections from one side thereof between upper and lower surfaces thereof and extending inwardly therein.

17. The structure set forth in claim 16 wherein said unit includes sealing means between the sections and spaced radially outward of and about said heating chamber and screw means releasably securing the sections together.

* * * * *